(12) United States Patent
Harsch

(10) Patent No.: US 12,140,472 B2
(45) Date of Patent: Nov. 12, 2024

(54) SYSTEM AND METHOD FOR ESTIMATING AN ACOUSTIC ATTENUATION OF A HEARING PROTECTION DEVICE

(71) Applicant: SONOVA AG, Staefa (CH)

(72) Inventor: Samuel Harsch, Lignieres (CH)

(73) Assignee: Sonova AG, Staefa (CH)

( * ) Notice: Subject to any disclaimer, the term of this patent is extended or adjusted under 35 U.S.C. 154(b) by 101 days.

(21) Appl. No.: 17/719,963

(22) Filed: Apr. 13, 2022

(65) Prior Publication Data
US 2022/0333978 A1    Oct. 20, 2022

(30) Foreign Application Priority Data

Apr. 15, 2021    (EP) .................................... 21168588

(51) Int. Cl.
*G01H 15/00*    (2006.01)
*A61F 11/08*    (2006.01)
(Continued)

(52) U.S. Cl.
CPC ........... *G01H 15/00* (2013.01); *A61F 11/085* (2022.01); *H04R 3/00* (2013.01); *H04R 11/02* (2013.01);
(Continued)

(58) Field of Classification Search
CPC ........ A61F 11/08; A61F 11/085; H04R 25/70; H04R 29/00; H04R 29/004; H04R 29/008;
(Continued)

(56) References Cited

U.S. PATENT DOCUMENTS

| 2,044,807 A | 6/1936 | Noyes |
| 3,968,334 A | 7/1976 | Padilla |

(Continued)

FOREIGN PATENT DOCUMENTS

| EP | 2317773 B1 | 7/2012 |
| EP | 2661910 B1 | 7/2016 |

(Continued)

OTHER PUBLICATIONS

"Extended European Search Report received in EP Application No. 21168588.8 on Oct. 12, 2021".

(Continued)

*Primary Examiner* — Carolyn R Edwards
*Assistant Examiner* — Kuassi A Ganmavo
(74) *Attorney, Agent, or Firm* — ALG Intellectual Property, LLC

(57) ABSTRACT

There is provided a system for estimating a total acoustic attenuation of a hearing protection device including an interface at a distal end and a sound canal extending from the interface to a sound opening at a medial end of the hearing protection device. The system comprises: a measurement unit including a loudspeaker and a microphone and being attachable to the interface in such a manner that, when the hearing protection device is worn in an ear canal of a user, the loudspeaker and the microphone are in acoustic communication, via the sound canal of the hearing protection device; a control unit configured to provide the loudspeaker with test audio signals to generate test sounds in the occluded ear canal volume and to receive test response audio signals captured by the microphone from the test sounds; and an evaluation unit configured to estimate a leakage acoustic impedance.

15 Claims, 6 Drawing Sheets

(51) Int. Cl.
*H04R 3/00* (2006.01)
*H04R 11/02* (2006.01)
*H04R 25/00* (2006.01)
*H04R 29/00* (2006.01)

(52) U.S. Cl.
CPC ............ *H04R 29/001* (2013.01); *A61F 11/08* (2013.01); *H04R 25/70* (2013.01); *H04R 29/008* (2013.01); *H04R 2460/15* (2013.01)

(58) Field of Classification Search
CPC .... H04R 2460/15; H04R 25/604; H04R 3/00; H04R 11/02; H04R 29/001; H04R 25/652; G01H 15/00
See application file for complete search history.

(56) References Cited

U.S. PATENT DOCUMENTS

| | | | | |
|---|---|---|---|---|
| 4,289,143 | A * | 9/1981 | Canavesio | G01H 15/00 73/585 |
| 6,567,524 | B1 * | 5/2003 | Svean | A61F 11/08 381/317 |
| 9,167,365 | B2 | 10/2015 | Voix et al. | |
| 2005/0123146 | A1 * | 6/2005 | Voix | A61F 11/08 381/328 |
| 2005/0126845 | A1 * | 6/2005 | Vaudrey | A61F 11/14 181/129 |
| 2005/0244026 | A1 * | 11/2005 | Nielsen | H04R 25/652 381/380 |
| 2006/0045284 | A1 * | 3/2006 | Haussmann | A61F 11/08 381/72 |
| 2006/0188105 | A1 * | 8/2006 | Baskerville | A61F 11/08 381/328 |
| 2012/0305329 | A1 * | 12/2012 | Keady | A61F 11/08 181/135 |
| 2014/0146989 | A1 * | 5/2014 | Goldstein | A61F 11/10 381/380 |
| 2014/0321657 | A1 * | 10/2014 | Stirnemann | H04R 25/606 381/60 |
| 2016/0241967 | A1 * | 8/2016 | Van 't Hof | H04R 25/30 |
| 2016/0295311 | A1 * | 10/2016 | Keady | A61F 11/10 |
| 2016/0295318 | A1 * | 10/2016 | Jankovsky | H04R 1/34 |
| 2017/0245787 | A1 * | 8/2017 | Brown | H04R 3/005 |
| 2018/0054670 | A1 * | 2/2018 | Struzik | G10K 11/17861 |
| 2020/0214601 | A1 | 7/2020 | Brown et al. | |
| 2020/0359125 | A1 * | 11/2020 | Henry | H04R 1/1066 |
| 2021/0289297 | A1 * | 9/2021 | Souviraa-Labastie | H04S 7/304 |
| 2021/0306779 | A1 * | 9/2021 | Knudsen | H04R 25/602 |

FOREIGN PATENT DOCUMENTS

| | | |
|---|---|---|
| EP | 3248577 A1 | 11/2017 |
| EP | 3053358 B1 | 12/2018 |
| WO | 2019092624 A1 | 5/2019 |

OTHER PUBLICATIONS

Van 't Hof, et al., "Testing of Musician's Earplugs", Conference: 2018 AES International Conference on Music Induced Hearing Disorders; AES, 60 East 42nd Street, Room 2520 New York 10165-2520 XP040698915, entire document, Jun. 11, 2018.

* cited by examiner

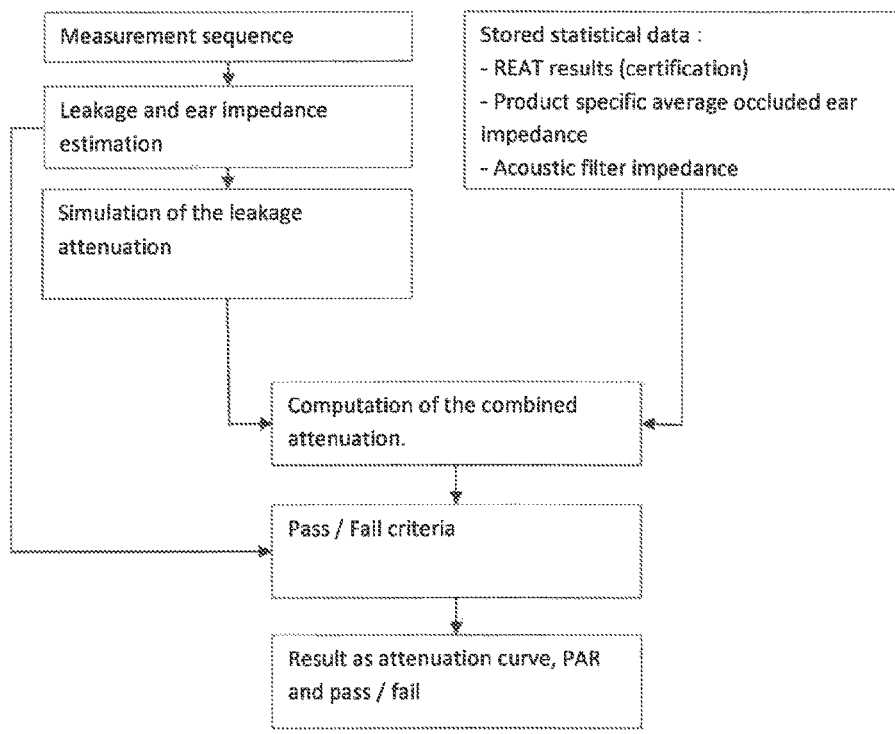
Fig. 10
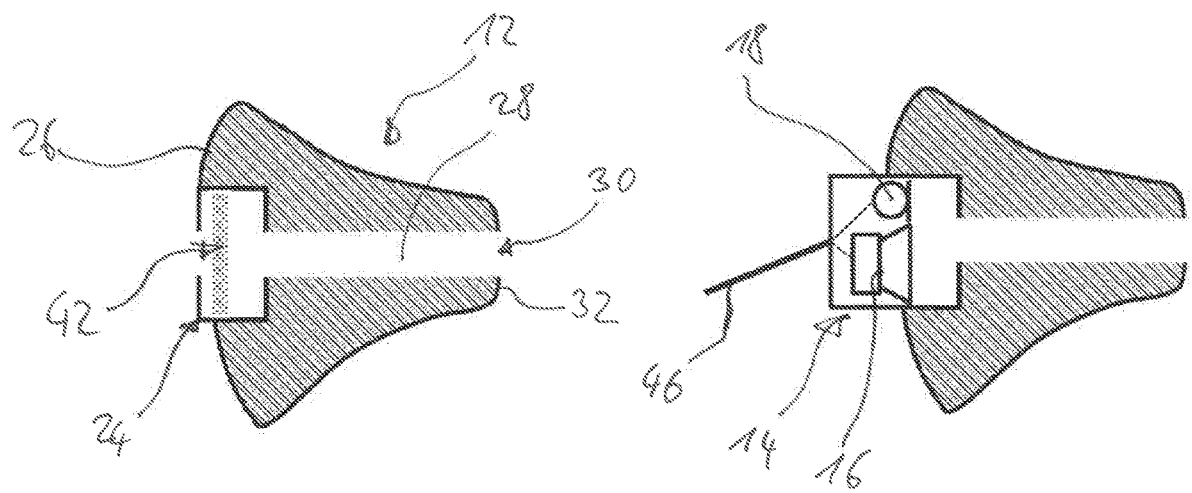
FIG. 1A
FIG. 1B

SYSTEM AND METHOD FOR ESTIMATING AN ACOUSTIC ATTENUATION OF A HEARING PROTECTION DEVICE

RELATED APPLICATIONS

The present application claims priority to EP Patent Application No. EP21168588, filed Apr. 15, 2021, the contents of which are hereby incorporated by reference in their entirety.

BACKGROUND INFORMATION

The use of hearing protection devices requires some monitoring of the individual acoustic attenuation achieved when the user is wearing the hearing protection device. This is particularly important for customized hearing protection devices which have been adapted to the individual user, typically by shaping the hearing protection device according to the measured individual shape of the user's ear channel. When customized hearing protection devices are delivered to the customer, the actual fitting within the ear channel should be tested in order to ensure that the required individual attenuation is actually achieved. Such fitting test has to be conducted for each individual user.

Measurement systems for conducting such field tests are known under the designation FAES (Field Attenuation Estimation System). Different kinds of FAES are known. One type of systems conducts REAT (Real Attenuation at Threshold) tests wherein the hearing threshold of the individual user is evaluated at a few frequencies when wearing the hearing protection device and when not wearing the hearing protection device, respectively, wherein typically headphones are used for producing the test sound to be perceived by the user. An example of such system is described in U.S. Pat. No. 3,968,334.

Certified REAT tests are conducted in specialized labs, wherein the hearing threshold of at least 16 persons is measured with the hearing protection device being worn and without the hearing protection device being worn, respectively, wherein test sounds are generated to speakers and the test persons have to push a button when they hear the sound, with the tests being done at 125, 250, 500, 1000, 2000, 4000 and 8000 Hz. The results of the 16 test persons are averaged, and the difference between the curve obtained without the hearing protection device being worn and the curve obtained with the hearing protection device being worn is representative of the average attenuation achieved by the hearing protection device in dB, which values are given in dB in a certification report of the respective hearing protection device.

Another type of FAES uses a binaural loudness balance method, wherein the user wears the hearing protection device only in one ear, while a test sound is provided by a headphone on both ears, wherein the user tries to adjust the level balance until there is the feeling of the same sound level on both ears. The same procedure then is repeated with the other ear. An example of such method is described in EP 3 248 577 A1.

While the test methods described so far are subjective methods in the sense that they require user feedback, there are also objective test methods. One example is a method known as F-MIRE (Field Microphone in Real Ear), wherein the hearing protection device is provided with an interface for receiving a first microphone which is connected via a sound channel of the hearing protection device to the residual ear channel volume when the hearing protection device is worn in the ear channel (during normal use of the hearing protection device the interface may receive a detachable acoustic filter for closing the outer end of the sound channel). A second microphone is placed outside the ear, typically close to the hearing protection device, and a test sound is generated outside the ear by a loudspeaker or a headphone. An attenuation provided by the hearing protection device is calculated from the difference between the audio signals captured by the first and second microphone. The measured signals typically are in the range of 125 Hz/8 kHz in octave bands in order to match with certified REAT measurement values. The obtained measurement values are a real attenuation value in dB, but since the microphones are not placed at the position of the ear drum, some correction factors have to be applied in the computation to compare the F-MIRE measurement values with the REAT values. Examples of F-MIRE measurements are described in EP 2 044 807 B1, U.S. Pat. No. 9,167,365 B2 and US 2020/0214601 A1.

Another objective test method uses leakage measurement. Also in this case, like in F-MIRE measurements, the hearing protection device comprises an interface which is connected via a sound channel to the residual ear volume when the hearing protection device is worn in the ear channel. The interface is configured to receive, for a leakage measurement, a measurement probe including a microphone and a miniature speaker which are connected via the sound channel to the residual ear channel volume when having been inserted into the interface. When conducting a leakage measurement, the speaker is supplied with test audio signals so as to generate a test sound (typically at low frequencies) within the occluded ear channel which is captured by the microphone so as to provide a test response audio signal. The measured test response audio signal is compared to a stored calibrator response audio signal obtained from a completely sealed residual ear channel volume. When there is no leakage of the hearing protection device (i.e., when the fit is perfect), the sound pressure in the occluded residual ear channel volume will be maximum and thus will match with the sound pressure obtained with the calibrator from a fully sealed volume. However, when there is significant leakage, the measured sound pressure in the occluded residual ear channel volume will drop at low frequencies, typically below 150 Hz. By analyzing the low frequency roll-off of the measured test response audio signal, compared to the calibrator reference measurement, the measurement system may evaluate whether the leakage is still acceptable or not, i.e., is below or above a certain given threshold and a pass/fail result may be output based on such leakage measurement.

Examples of leakage measurement systems are described in EP 3 053 358 B1, EP 2 317 773 B1, EP 2 661 910 B1 and WO 2019/092624 A1.

BRIEF DESCRIPTION OF THE DRAWINGS

Hereinafter, examples of the invention will be illustrated by referenced to the attached drawings, wherein:

FIGS. 1A and 1B are schematic views of a hearing protection device during normal use with an acoustic filter and during an attenuation measurement wherein the filter is replaced by a measurement unit, respectively;

FIG. 10 is a flow diagram illustrating an example of a method for estimating the total acoustic attenuation provided by a hearing protection device.

DETAILED DESCRIPTION

Figure 2:
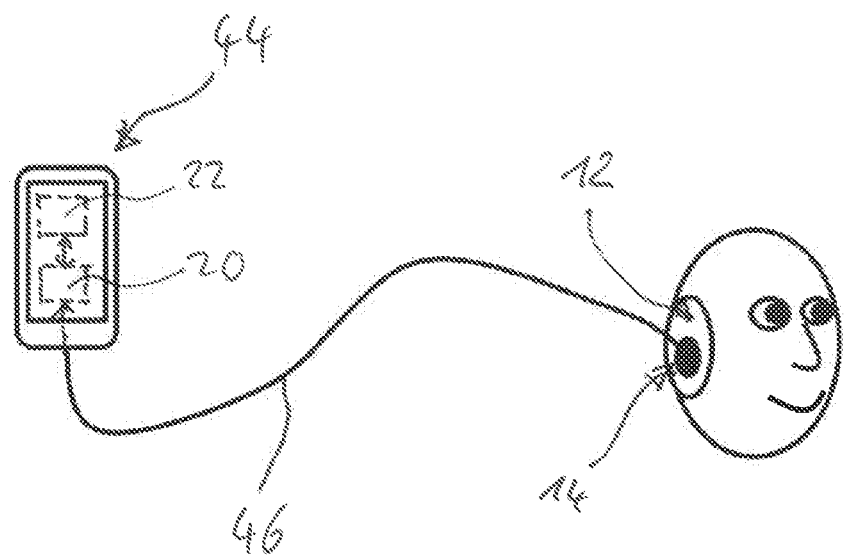
FIG. 2 is a schematic illustration of the hearing protection device during an attenuation measurement, wherein the measurement unit is connected to an external device.

Described herein are a system and method for estimating an acoustic attenuation of a hearing protection device.

In some embodiments, a system and method are provided for estimating a total acoustic attenuation of a hearing protection device of a given type, when worn in the ear channel, which is both relatively simple and reliable.

The embodiments described herein are beneficial in that, by combining a leakage measurement approach with predetermined statistical data related to an acoustic attenuation provided by the given type of hearing protection device, a setup may be used which is simple and has a relatively small size and which allows for a relatively fast measurement with relatively low sensitivity to background noise (like a typical leakage tester), while nevertheless providing for an estimation of total acoustic attenuation provided by the individual hearing protection device when worn in the ear channel of the user. Stated otherwise, the present embodiments combine the benefits of a leakage tester with the benefits of F-MIRE tests.

According to one embodiment, the predetermined statistical data includes at least one of: REAT (Real Ear Attenuation at Threshold) values measured for said type of hearing protection device; an acoustic impedance of an acoustic filter to be used with said type of hearing protection device; REAT values measured for the type of hearing protection device when being used with a detachable acoustic filter; and a measured average of an occluded ear impedance of humans wearing said type of hearing protection device.

According to one embodiment, the evaluation unit is configured to estimate the leakage acoustic impedance by comparing the received test response audio signals to respective predetermined calibrator test response audio signals obtained when using the measurement unit with a fully sealed calibrator chamber so as to generate and capture the respective test sounds in a fully sealed calibrator volume simulating the occluded residual ear canal volume.

According to one embodiment, the evaluation unit is configured to determine a total acoustic impedance from the received test response audio signals, wherein the determined total acoustic impedance may correspond to a parallel connection of the leakage acoustic impedance and an occluded ear acoustic impedance.

According to one embodiment, the evaluation unit is configured to estimate an occluded ear impedance from the received test response audio signals and from calibrator response audio signals, wherein the evaluation unit may be configured to estimate a leakage acoustic attenuation corresponding to a transfer function from outside the ear to the occluded residual volume of the ear canal from a simulation in which the estimated leakage impedance is loaded by the estimated occluded ear impedance. The evaluation unit may be configured to estimate the total acoustic attenuation provided by the hearing protection device from the estimated leakage acoustic attenuation and the predetermined statistical data. The evaluation unit may be further configured to estimate an occluded ear volume from the estimated occluded ear impedance.

According to one embodiment the evaluation unit is configured to estimate the total acoustic attenuation provided by the hearing protection device as a function of frequency.

According to one embodiment, the evaluation unit is configured to judge whether the hearing protection device is useable or not based on the estimated total acoustic attenuation provided by the hearing protection device and/or on the estimated leakage acoustic impedance.

According to one embodiment, the evaluation unit is configured to derive a PAR (Personal Attenuation Rating) from the total acoustic attenuation provided by the hearing protection device.

According to one embodiment, the system further comprises an output unit communicatively coupled to the evaluation unit for outputting evaluation results obtained by the evaluation unit to a user.

According to one embodiment, the test audio signal is a sine sweep signal, a noise signal, an MLS sequence signal or a multi-tone signal.

According to one embodiment, the loudspeaker is a balanced armature speaker and/or has an output impedance of at least $100*10^6$ N*s/m$^5$ at 200 Hz and $600*10^6$ N*s/m$^5$ at 30 Hz.

According to one embodiment, the measurement unit comprises a second microphone, wherein the measurement unit may comprise an acoustic resistor placed between the two microphones.

According to one embodiment, the control unit and/or the evaluation unit is implemented in computation device, such as a PC, or in a mobile device, such as tablet computer or a smartphone, which is configured to be communicatively connected to the measurement unit.

According to one embodiment, the hearing protection device is customized according to an individual shape of the user's ear canal).

According to one embodiment, the interface the hearing protection device is configured to receive a detachable acoustic filter during times when the measurement unit is not attached to the interface.

A "hearing protection device" as used hereinafter is any ear worn device which provides for a certain acoustic attenuation by sealing the ear canal at least to some extent. A "type of hearing protection device" as used hereinafter is a class of hearing protection devices which are identical apart from individual adaptations, like a customized shape.

A "distal end" (or "outer end") of the hearing protection device as used hereinafter is that end which is farther away (or which faces away) from the tympanic membrane when the hearing protection device is worn in the ear canal, while a "medial end" (or "inner end") of the hearing protection device is that end which is closer to (or which faces) the tympanic membrane.

"Attenuation" as used hereinafter generally refers to an acoustic attenuation even if not explicitly mentioned.

Figure 3:
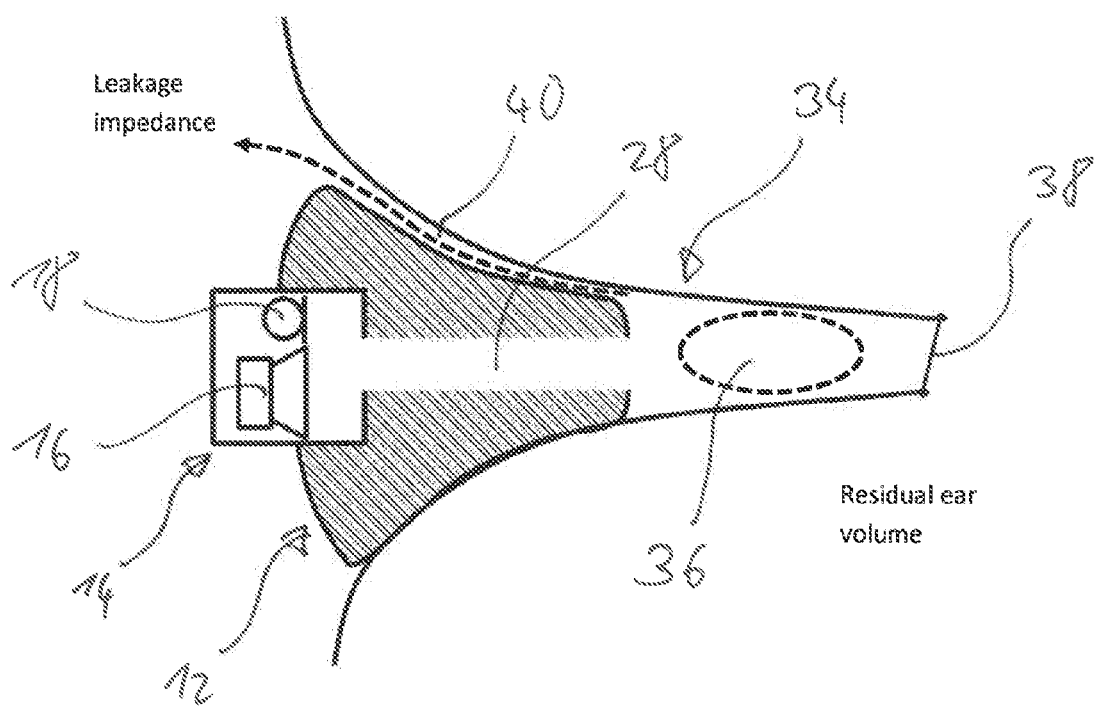
FIG. 3 is a schematic longitudinal sectional view of the hearing protection device during an attenuation measurement, when inserted into a user's ear channel.

FIGS. 1 to 3 illustrate schematically an example of a system 10 for estimating an acoustic attenuation of a hearing protection device 12. The system comprises a measurement unit 14 including a loudspeaker 16 and a microphone 18, a control unit 20 to be communicatively coupled with the measurement unit 14, and an evaluation unit 22 communicatively coupled with the control unit 20.

The hearing protection device 12 comprises an interface 24 at an outer or distal end 26 and a sound channel 28 extending from the interface to a sound opening 30 at an inner or medial end 32 of the hearing protection device 12. The hearing protection device 12 is shaped to be worn in a user's ear channel 34 and may be designed, for example, as a hearing protection ear plug. In some implementations, the hearing protection device 12 may be customized according to the individual shape of the user's ear channel 34, so that the outer shape of the hearing protection device is adapted to the individual inner shape of the ear channel 34 for optimizing fit of the hearing protection device 12.

When the hearing protection device 12 is worn in the ear channel 34, an occluded residual ear volume 36 is created between the inner end 32 of the hearing protection device 12 and the ear drum 38. In cases in which there is no optimal fit of the hearing protection device there may be a leakage path 40 between the wall of the ear channel 34 and the hearing protection device 12, leading from the occluded residual ear volume 36 past the hearing protection device 12 to ambience.

The interface 24 is configured to receive the measurement unit 14 so as to temporarily attach the measurement unit 14 to the hearing protection device 12 for conducting acoustic attenuation measurements. When the measurement unit 14 is attached to the hearing protection device 12 worn in the ear channel 34, the loudspeaker 16 and the microphone 18 are in acoustic communication, via the sound channel 28 of the hearing protection device 12, with the residual ear channel volume 36 being occluded by the hearing protection device 12, as illustrated in FIG. 3.

In some implementations, the interface 24 may receive an acoustic filter 42 during times when the measurement unit 14 is not attached to the interface 24, i.e., during normal practical use of the hearing protection device 12, as illustrated in FIG. 1A.

In some implementations, the loudspeaker 16 may be a miniature loudspeaker, and, in particular, it may be a balanced armature speaker. The loudspeaker may have a high output impedance, such as at least $100*10^6$ N*s/m$^5$ at 200 Hz and $600*10^6$ N*s/m$^5$ at 30 Hz, (these minimum values are equivalent to the occluded ear impedance), for example $2.5*10^9$ N*s/m$^5$ at 200 Hz and $15*10^9$ N*s/m$^5$ at 30 Hz (such values are close to a volume-velocity source). In some implementations, the measurement unit 14 may comprise a second microphone, wherein an acoustic resistor may be placed between the two microphones, in order to achieve a more accurate measurement of the acoustic impedance.

In some implementations, the control unit 20 and/or the evaluation unit 22 may be implemented in a computation device, such as a PC, or in a mobile device, such as a tablet computer or a smartphone, which is configured to be communicatively coupled to the measurement unit 12.

In the example of FIG. 2, the control unit 20 and the evaluation unit 22 are implemented in a smartphone 44 which is connected to the measurement unit 12 via a cable connection 46. For example, the control unit 20 and the evaluation unit 22 may be functionally implemented as an app running on the smartphone processor.

The control unit 20 is configured to provide the loudspeaker 16 with test audio signals so as to generate test sounds in the occluded ear channel volume 34, from which the microphone 18 captures test response audio signals which are supplied to the control unit 20. The evaluation unit 22 is configured to estimate a total attenuation provided by the hearing protection device 12 when worn in the ear channel 34 from the received test response audio signals and from predetermined statistical data related to an acoustic attenuation provided by the type of hearing protection devices to which the hearing protection device 12 belongs to.

In some implementations, the predetermined statistical data may include at least one of REAT values measured for the respective type of hearing protection device (this could be from a certification of the type of hearing protection device), an acoustic impedance of an acoustic filter to be used in practice with the type of hearing protection device (this allows to adapt the estimated total attenuation provided by the hearing protection device according to the specific acoustic filter used with the individual hearing protection device of that type; in this case, REAT values measured for the type of hearing protection device with a full-block filter will be used, together with the acoustic impedance of the specific acoustic filter to be used in practice with the type of hearing protection device (this specific acoustic filter usually will not be a full-block filter), REAT values measured for the type of hearing protection device when including a specific acoustic filter (namely the filter which is used in practice with the individual hearing protection device), and a measured average of an occluded ear impedance (or an occluded ear residual ear channel volume) of humans wearing the type of hearing protection device.

The measurements conducted by the measurement unit 14 allow to estimate the individual leakage of the hearing protection device 12 within the ear channel 34 from the test response audio signals captured by the microphone 18 from the test sounds generated by the speaker 16.

In some implementations, the test audio signals cover a certain frequency range, such as from 10 Hz to 1 kHz, wherein the test audio signals may include, for example, a sine sweep signal, a noise signal, an MLS (maximum length sequence) sequence signal or a multi-tone signal.

A leakage acoustic impedance may be estimated from the captured response audio signals. This can be achieved, for example, by comparing the received captured test response audio signals to respective predetermined calibrator test response audio signals which are obtained when using the measurement unit 14 with a fully sealed calibrator chamber so as to generate and capture the respective test sounds in a fully sealed calibrator volume simulating the occluded residual ear channel volume 36. The use of calibrators in leakage measurement as such is known, for example from EP 3 053 358 B1. In cases in which there is no or only little leakage, the captured test response audio signals will be very similar to the predetermined/known test response audio signals obtained with the calibrator. In cases in which there is relatively large leakage the level of the captured test response audio signals typically will be significantly lower at relatively low frequencies below 150 Hz (low frequency roll-off), whereas at higher frequencies the impact of the leakage on the sound level will be lower.

Figure 4:
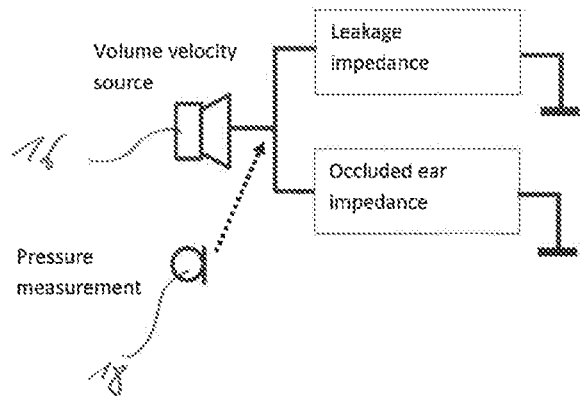
FIG. 4 is a schematic representation of the acoustic situation of the system of FIG. 3.

A schematic representation of the acoustic properties of the system shown in FIG. 3 is illustrated in FIG. 4, according to which the total acoustic impedance seen by the speaker 16 of the measurement unit 14 corresponds to a parallel connection of the leakage acoustic impedance (which is the acoustic impedance of the leakage path 40) and the occluded ear acoustic impedance (which is determined by the impedances of the residual ear volume 36, the sound channel 28 and the ear drum 38). It is noted that the speaker 16 due to its high output impedance may be considered as a volume-velocity source, so that the pressure captured by the microphone 18 is proportional to the total acoustic impedance which is determined by the leakage acoustic impedance and the occluded acoustic ear impedance.

The leakage impedance may be considered as an acoustic resistance, and the occluded ear impedance may be considered as an acoustic compliance.

Like the leakage acoustic impedance, also the occluded ear impedance may be estimated from the captured test response audio signals. As the air volume of the calibrator is known, the sound level difference at higher frequencies (about 150 Hz) between the calibrator and the measured ear is proportional to the air volume difference, while the leakage is estimated by the roll-off (comparison of levels at 150 Hz and at 30 Hz). There are various other methods, like estimating the complex acoustic impedance out of two microphones.

The calibrator has a known volume and no leak, and its acoustic impedance is known. Thus, a sound generated by the speaker at a known amplitude will have a predictable level e.g. at 30 Hz and at 150 Hz. Those levels may be measured and stored as reference for the known calibrator impedance. Then, if, for example, the same levels are measure in the ear as measured with the calibrator, this means that the ear impedance is the same as the calibrator. Any level variation at those frequencies is proportional to the ear impedance difference compared to the calibrator. Variation of ear volume impedance mainly affects levels at both frequencies compared to the calibrator levels, while leakage influences mainly the level at 30 Hz relative the level at 150 Hz (i.e., leakage affects the slope). Thus, the ear impedance may be estimated from a level difference between the measured in-ear level at 150 Hz and the calibrator level at 150 Hz. Leakage may be estimated from the measured level difference at 30 Hz and 150 Hz.

Figure 5:
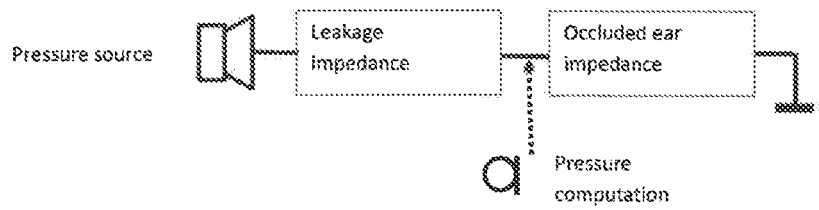
FIG. 5 is a schematic representation of the acoustic situation used in a simulation for estimating the attenuation provided by the hearing protection device.

The leakage acoustic attenuation corresponds to a transfer function from outside the ear to the occluded residual ear channel volume 36 and may be estimated from a simulation in which the estimated leakage impedance is loaded by the estimated occluded ear impedance, as illustrated in FIG. 5. It is noted that in this case the source of a sound coming from outside of the ear (i.e., from ambience) could be considered as a pressure source.

Figure 6A:
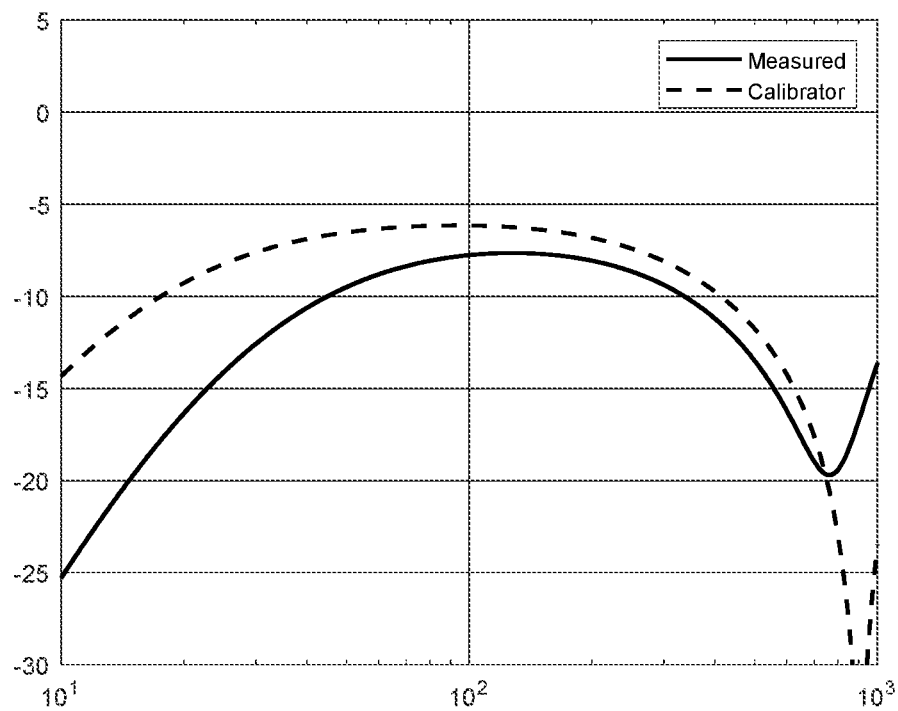
FIG. 6A shows an example of a measured sound pressure level in the occluded ear channel (solid line), together with a calibrator reference measurement (dashed line), versus frequency.
Figure 6B:
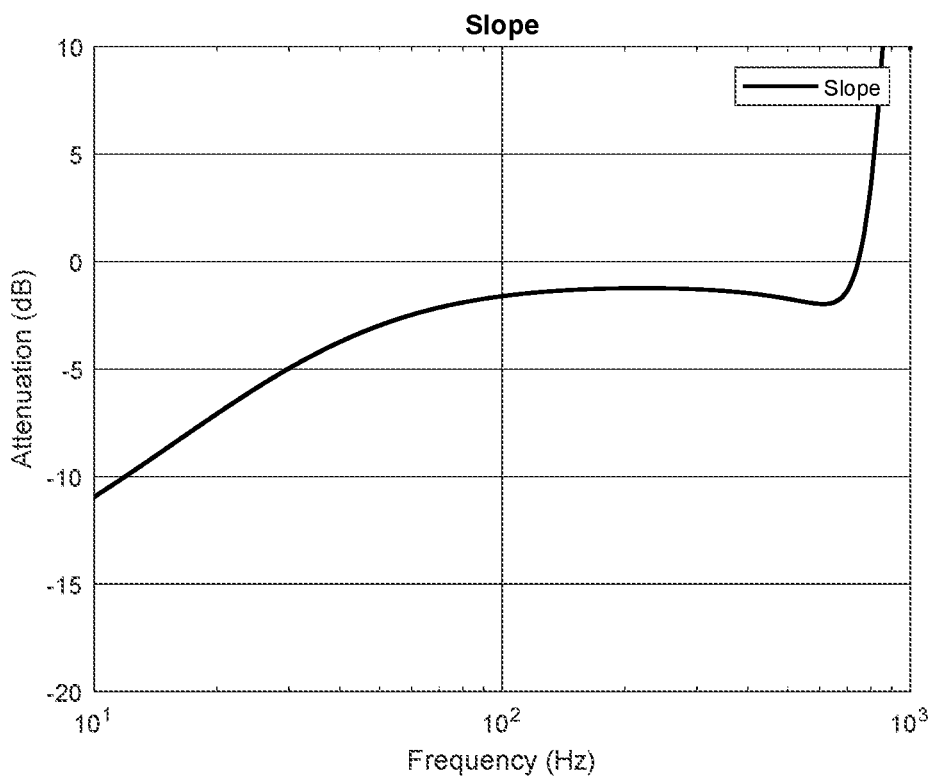
FIG. 6B shows the difference between the measured curve and the reference curve of FIGS. 6A.

FIG. 6A shows an example of the test sound pressure level versus frequency as measured by the microphone 18 (solid line) and the respective test sound pressure level obtained with a calibrator volume (dashed line); and in FIG. 6B the difference between the two curves of FIG. 6A is shown. As this example shows a hearing protection device 12 including a significant leakage path 40, it can be seen that there is a pronounced low frequency role off for frequencies below about 150 Hz.

Figure 7:
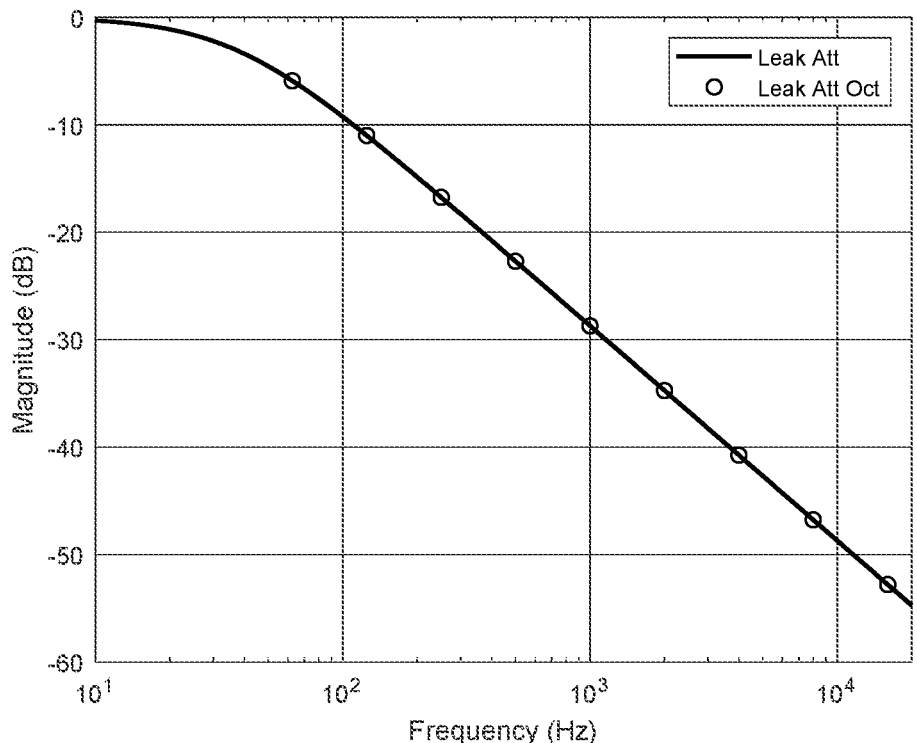
FIG. 7 is an example of the estimated leakage acoustic attenuation vs. frequency as obtained from the simulation of FIG. 5.

In FIG. 7 an example of the estimated leakage acoustic attenuation is shown as a function of frequency, as obtained from the simulation configuration shown in FIG. 5. It can be seen in FIG. 7 that at low frequencies below 150 Hz the attenuation is relatively low due to the leakage path 40.

Figure 8:
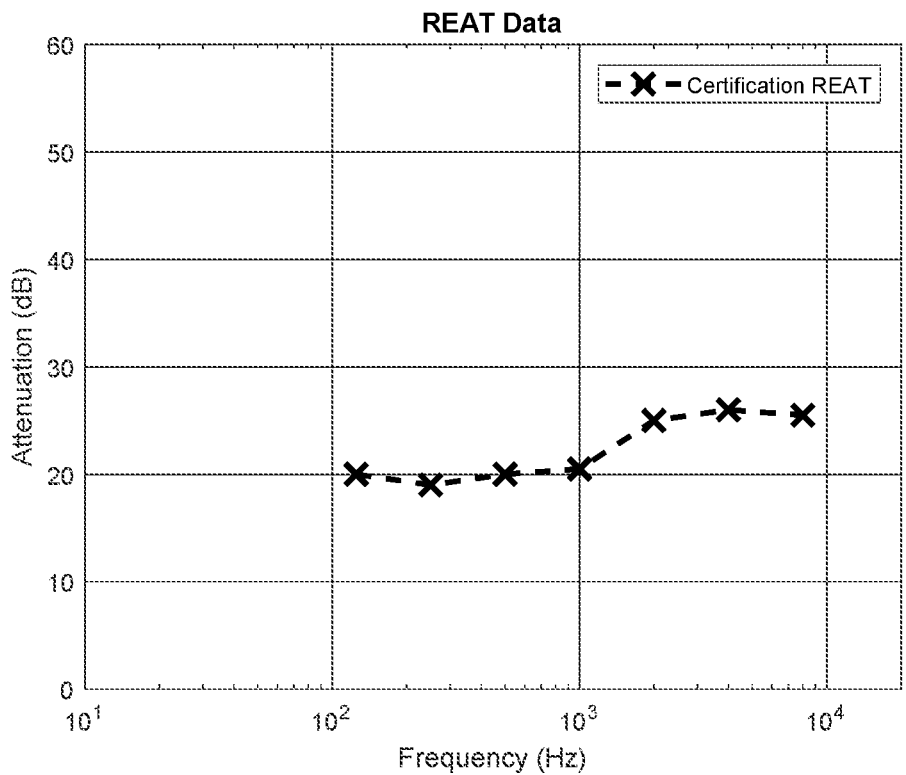
FIG. 8 is an example of REAT data for the type of hearing protection device of FIG. 1A.

As a next step, the total acoustic attenuation provided by the hearing protection device 12 when worn in the ear channel 34 can be estimated from the estimated leakage acoustic attenuation and predetermined statistical data relating to an acoustic attenuation provided by the given type of hearing protection device 12, which, for example, may be REAT data from the certification of the type of hearing protection device as illustrated in FIG. 8.

Figure 9A:
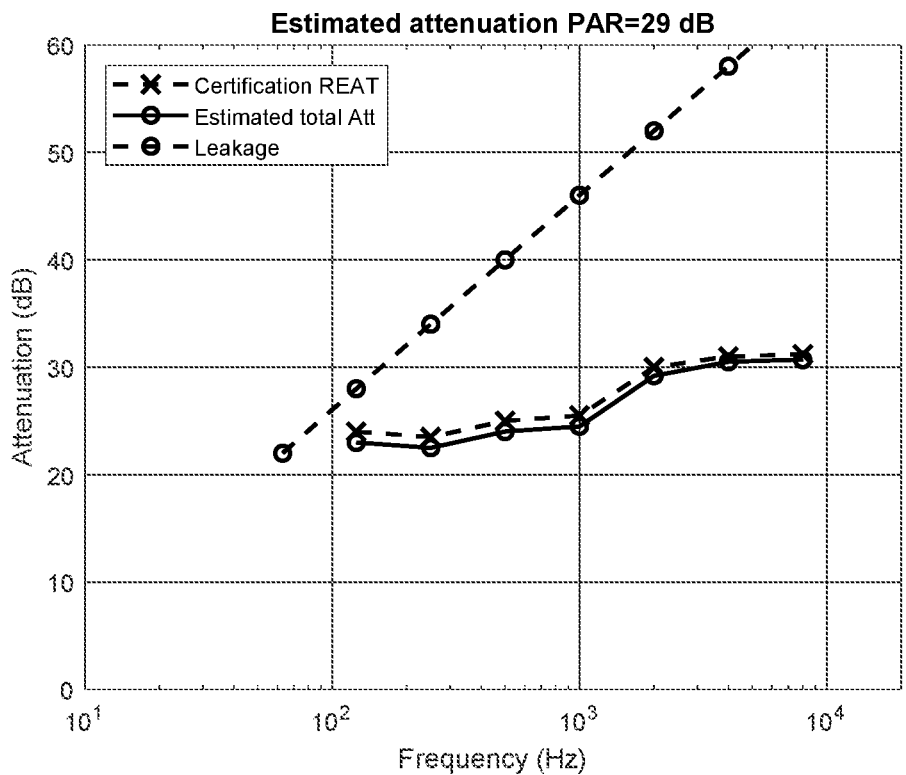
FIGS. 9A to 9C show examples of the leakage acoustic attenuation of FIG. 7, the REAT data of FIG. 8 and the resulting estimated total acoustic attenuation provided by the hearing protection device for a situation with little leakage, medium leakage and high leakage, respectively.
Figure 9B:
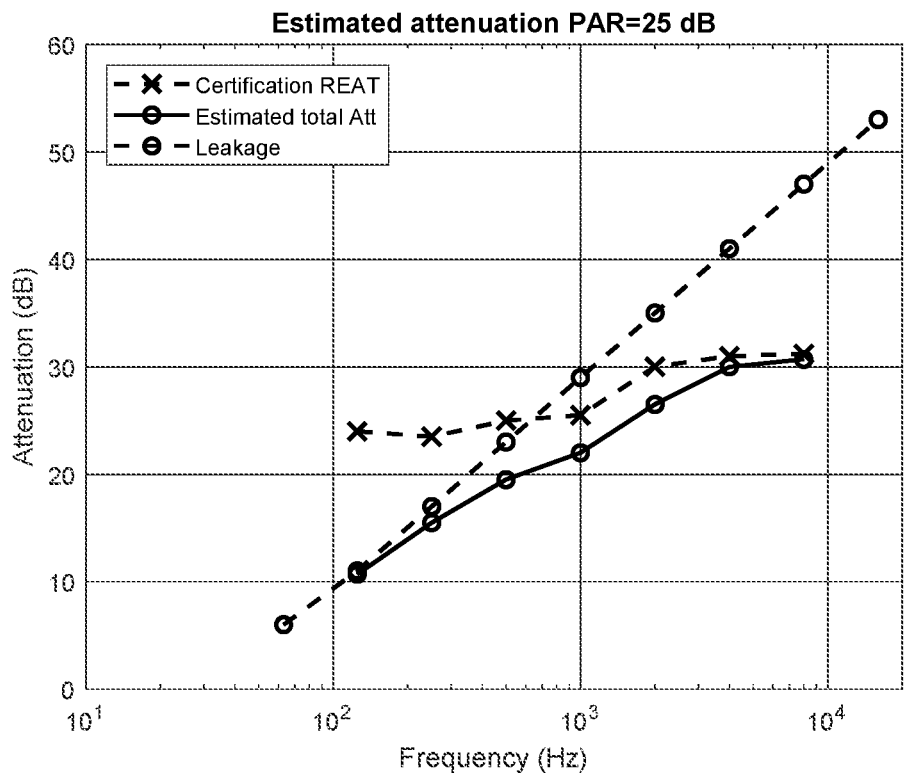
Figure 9C:
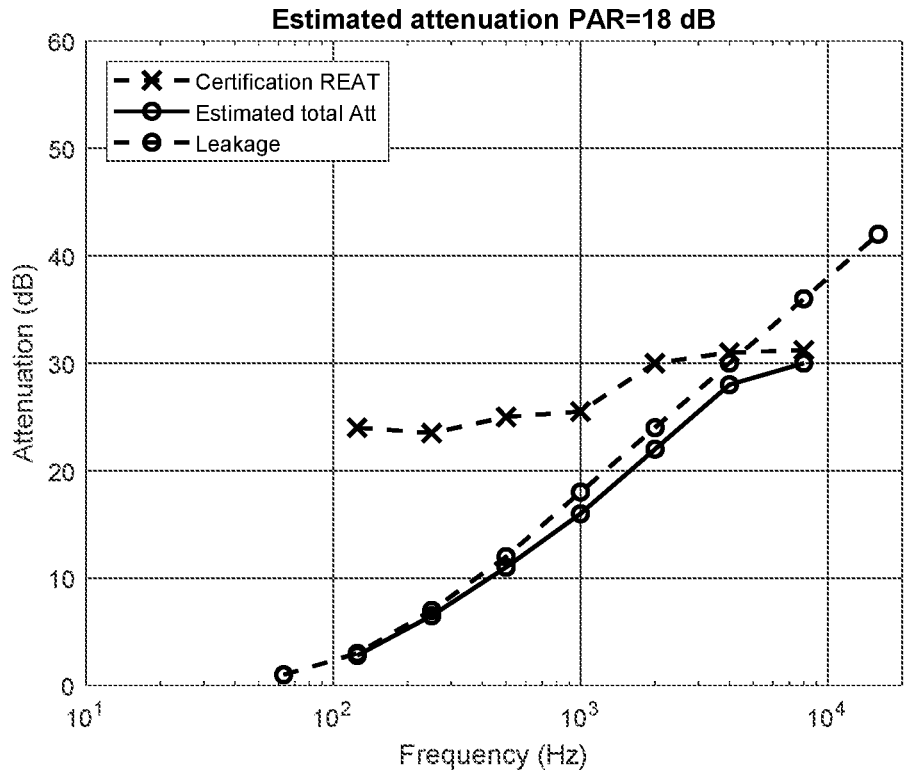

In FIGS. 9A to 9C examples of the estimated total acoustic attenuation, together with the estimated leakage acoustic attenuation and the REAT data, are shown versus frequency for a good fit, a medium fit and a bad fit, respectively. Accordingly, in FIG. 9A the estimated total acoustic attenuation equals almost the REAT data, whereas in FIGS. 9B and 9C the estimated total acoustic attenuation is significantly lower than the respective REAT data, in particular for medium and lower frequencies.

The acoustic attenuation estimation system may output the results of the attenuation estimation via an output unit communicatively coupled to the evaluation unit. In the example of FIG. 3 the output unit may be the display and/or the speaker of the mobile device 44. In some implementations, the system may output the total acoustic attenuation as a function of frequency, as shown in FIGS. 9A to 9C. Alternatively or in addition, the evaluation unit 22 may judge whether the hearing protection device 12 is usable or not based on the estimated total acoustic attenuation and/or on the estimated leakage acoustic impedance. For example, appropriate pass/fail criteria may be applied to output a judgement as to whether or not the hearing protection device is usable.

In other examples, the evaluation unit 22 may be configured to derive a PAR (Personal Attenuation Rating) from the estimated total attenuation, so as to output such PAR to the user.

Further, the evaluation unit 22 may be configured to estimate an occluded ear volume from the estimated occluded ear impedance (the total attenuation is also affected by the total residual volume in the ear; for example, large residual volumes give more attenuation for a same leak, due to lower load impedance; the system may use this data as well to compute the total attenuation).

In FIG. 10 a flow diagram of an example of an attenuation estimation method is shown.

While the features described herein are particularly suitable for customized hearing protection devices, it may be used also for universal fit hearing protection devices. The invention may be used not only for acoustic attenuation estimation of customized hearing protection devices, but also as an embedded fit check in hearables or active hearing protection devices (the system, in particular the measurement unit, may be integrated within an active hearing protection device), or as a fit check during the process of a self-fit customized hearing protection device (in a self-fit process a device like a hearing protector or a wireless headset can be shaped by the user himself or by a hearing care professional, for example by hardening a soft material directly within the ear using a UV light source built in the headset; the present invention may be used in such process to evaluate the acoustic attenuation during the customization process and/or to check the acoustic attenuation after the process, or as an optimization method for equalization (if the actual acoustic attenuation and leakage of the product, such as a wireless headset, when worn by the user is known, such information can be used to make an individual equalization of the frequency response to compensate for it) or compensation filters in hearables.

All measurement/estimation results may be stored by the system.

In some implementations, the measurement/estimation results may be used to adapt at least one filter coefficient of the hearing protection device.

What is claimed is:

1. A system for estimating a total acoustic attenuation of a hearing protection device of a given type including an interface at a distal end and a sound canal extending from the interface to a sound opening at a medial end of the hearing protection device, the system comprising:
    a measurement unit including a loudspeaker and a microphone and being attachable to the interface in such a manner that, when the hearing protection device is worn in an ear canal of a user, the loudspeaker and the microphone are in acoustic communication, via the sound canal of the hearing protection device, with a residual ear canal volume occluded by the hearing protection device,
    a control unit configured to be communicatively coupled with the measurement unit and to provide the loudspeaker with test audio signals to generate test sounds in the occluded ear canal volume and to receive test response audio signals captured by the microphone from the test sounds, and
    an evaluation unit configured
        to estimate a leakage acoustic impedance of a leakage path between a wall of the ear canal and the hearing protection device using the received test response audio signals, the leakage path connecting the residual ear canal volume to an outside of the ear canal,
        to estimate an occluded ear acoustic impedance, and
        to estimate the total acoustic attenuation provided by the hearing protection device using the estimated leakage acoustic impedance, the estimated occluded ear acoustic impedance and predetermined statistical data related to an acoustic attenuation provided by the given type of hearing protection device, the predetermined statistical data including REAT (Real Ear Attenuation at Threshold) values measured for other users for the type of hearing protection device when being used with a detachable acoustic filter.

2. The system of claim 1, wherein the predetermined statistical data further includes at least one of: REAT values measured for said type of hearing protection device; an acoustic impedance of an acoustic filter to be used with said type of hearing protection device; or a measured average of an occluded ear impedance of humans wearing said type of hearing protection device.

3. The system of claim 1, wherein the evaluation unit is configured to estimate the leakage acoustic impedance by comparing the received test response audio signals to respective predetermined calibrator test response audio signals obtained when using the measurement unit with a fully sealed calibrator chamber so as to generate and capture the respective test sounds in a fully sealed calibrator volume simulating the occluded residual ear canal volume.

4. The system of claim 1, wherein the evaluation unit is configured to determine a total acoustic impedance from the received test response audio signals.

5. The system of claim 4, wherein the determined total acoustic impedance corresponds to a parallel connection of the leakage acoustic impedance and an occluded ear acoustic impedance.

6. The system of claim 1, wherein the evaluation unit is configured to estimate an occluded ear impedance from the received test response audio signals and from calibrator response audio signals.

7. The system of claim 6, wherein the evaluation unit is configured to estimate a leakage acoustic attenuation corresponding to a transfer function from outside the ear to the occluded residual volume of the ear canal from a simulation in which the estimated leakage acoustic impedance is loaded by the estimated occluded ear impedance.

8. The system of claim 7, wherein the evaluation unit is configured to estimate the total acoustic attenuation provided by the hearing protection device from the estimated leakage acoustic attenuation and the predetermined statistical data.

9. The system of claim 6, wherein the evaluation unit is configured to estimate an occluded ear volume from the estimated occluded ear impedance.

10. The system of claim 1, wherein the evaluation unit is configured to estimate the total acoustic attenuation provided by the hearing protection device as a function of frequency.

11. The system of claim 1, wherein:
    the evaluation unit is configured to at least one of:
        judge whether the hearing protection device is useable or not based at least one of on the estimated total acoustic attenuation provided by the hearing protection device and on the estimated leakage acoustic impedance; and
        derive a PAR (Personal Attenuation Rating) from the total acoustic attenuation provided by the hearing protection device.

12. The system of claim 1, wherein the loudspeaker at least one of is a balanced armature speaker and has an output impedance of least $100*10^6$ N*s/m5 at 200 Hz and $600*10^6$ N*s/m5 at 30 Hz.

13. The system of claim 1, wherein at least one of the control unit and the evaluation unit is implemented in computation device configured to be communicatively connected to the measurement unit.

14. The system of claim 1, further comprising the hearing protection device, wherein at least one of the hearing protection device is customized according to an individual shape of the user's ear canal, and the interface of the hearing protection device is configured to receive a detachable acoustic filter during times when the measurement unit is not attached to the interface.

15. A method of estimating a total acoustic attenuation of a hearing protection device of a given type including an interface at a distal end and a sound canal extending from the interface to a sound opening at a medial end of the hearing protection device, the method comprising:
    attaching a measurement unit including a loudspeaker and a microphone to the interface;
    inserting the hearing protection device into an ear canal of a user, so that the loudspeaker and the microphone are in acoustic communication, via the sound canal of the hearing protection device, with a residual ear canal volume occluded by the hearing protection device, providing the loudspeaker with test audio signals to generate test sounds in the occluded ear canal volume;
    receiving test response audio signals captured by the microphone from the test sounds;

estimating a leakage acoustic impedance of a leakage path between a wall of the ear canal and the hearing protection device from the received response audio signals, the leakage path connecting the residual ear canal volume to an outside of the ear canal; and estimating a total acoustic attenuation provided by the hearing protection device from the estimated leakage acoustic impedance, taking into account predetermined statistical data related to an acoustic attenuation provided by the given type of hearing protection device, the predetermined statistical data including REAT (Real Ear Attenuation at Threshold) values measured for other users for the type of hearing protection device when being used with a detachable acoustic filter.

* * * * *